US012685577B2

(12) United States Patent
Nott et al.

(10) Patent No.: US 12,685,577 B2
(45) Date of Patent: *Jul. 21, 2026

(54) COMBINATION ULTRASONIC AND ELECTROSURGICAL INSTRUMENT WITH ADJUSTABLE ENERGY MODALITIES AND METHOD FOR LIMITING BLADE TEMPERATURE

(71) Applicant: Cilag GmbH International, Zug (CH)

(72) Inventors: Cameron R. Nott, Loveland, OH (US); Amrita S. Sawhney, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 339 days.

This patent is subject to a terminal disclaimer.

(21) Appl. No.: 18/350,329

(22) Filed: Jul. 11, 2023

(65) Prior Publication Data

US 2023/0346447 A1 Nov. 2, 2023

Related U.S. Application Data

(63) Continuation of application No. 17/572,003, filed on Jan. 10, 2022, now Pat. No. 11,737,804, which is a
(Continued)

(51) Int. Cl.
*A61B 18/14* (2006.01)
*A61B 17/32* (2006.01)
(Continued)

(52) U.S. Cl.
CPC ...... *A61B 18/00* (2013.01); *A61B 17/320092* (2013.01); *A61B 18/1233* (2013.01);
(Continued)

(58) Field of Classification Search
CPC .... A61B 17/320068; A61B 17/320092; A61B 2017/00026; A61B 2017/00084;
(Continued)

(56) References Cited

U.S. PATENT DOCUMENTS

| 5,322,055 | A | 6/1994 | Davison et al. |
| 5,792,135 | A | 8/1998 | Madhani et al. |

(Continued)

FOREIGN PATENT DOCUMENTS

| CN | 101045015 A | 10/2007 |
| CN | 102497827 A | 6/2012 |

(Continued)

OTHER PUBLICATIONS

Chinese Search Report dated Oct. 9, 2022, for Application No. 201880033823.0, 1 page.
(Continued)

*Primary Examiner* — Khadijeh A Vahdat
(74) *Attorney, Agent, or Firm* — FBT Gibbons LLP

(57) ABSTRACT

An ultrasonic surgical instrument and method of limiting an ultrasonic blade temperature includes adjusting at least one power parameter of the ultrasonic energy in response to reaching a predetermined frequency parameter change threshold in the ultrasonic blade limiting the temperature of the ultrasonic blade to an upper temperature limit. The ultrasonic surgical instrument further includes an end effector having an ultrasonic blade, a jaw, and a controller. The jaw is movably positioned relative to the ultrasonic blade and configured to move between an open position and a closed position. The controller operatively connects to the ultrasonic blade and is configured to measure an ultrasonic frequency of the ultrasonic blade. The controller has a memory including a plurality of predetermined data correlations that correlate changes in measured ultrasonic frequency of the ultrasonic blade to a blade temperature of the ultrasonic blade.

20 Claims, 5 Drawing Sheets

Related U.S. Application Data continuation of application No. 15/967,775, filed on May 1, 2018, now Pat. No. 11,229,474.

(60) Provisional application No. 62/509,336, filed on May 22, 2017.

(51) Int. Cl.
| | |
|---|---|
| *A61B 18/00* | (2006.01) |
| *A61B 18/12* | (2006.01) |
| *A61B 17/00* | (2006.01) |
| *A61B 90/00* | (2016.01) |

(52) U.S. Cl.
CPC ............... *A61B 18/1445* (2013.01); *A61B 2017/00026* (2013.01); *A61B 2017/00084* (2013.01); *A61B 2017/00106* (2013.01); *A61B 2017/0019* (2013.01); *A61B 2017/00526* (2013.01); *A61B 2017/320075* (2017.08); *A61B 2017/320088* (2013.01); *A61B 2017/320094* (2017.08); *A61B 2017/320095* (2017.08); *A61B 2018/00607* (2013.01); *A61B 2018/0063* (2013.01); *A61B 2018/00642* (2013.01); *A61B 2018/00648* (2013.01); *A61B 2018/00654* (2013.01); *A61B 2018/00672* (2013.01); *A61B 2018/00678* (2013.01); *A61B 2018/00702* (2013.01); *A61B 2018/00708* (2013.01); *A61B 2018/00714* (2013.01); *A61B 2018/00755* (2013.01); *A61B 2018/00761* (2013.01); *A61B 2018/00779* (2013.01); *A61B 2018/00875* (2013.01); *A61B 2018/00916* (2013.01); *A61B 2018/00928* (2013.01); *A61B 2018/00994* (2013.01); *A61B 2018/126* (2013.01); *A61B 2018/1452* (2013.01); *A61B 2090/064* (2016.02)

(58) Field of Classification Search
CPC .. A61B 2017/00106; A61B 2017/0019; A61B 2017/00526; A61B 2017/320075; A61B 2017/320088; A61B 2017/320094; A61B 2017/320095; A61B 18/00; A61B 18/1233; A61B 18/1442; A61B 18/1445; A61B 2018/00607; A61B 2018/0063; A61B 2018/00642; A61B 2018/00648; A61B 2018/00654; A61B 2018/00672; A61B 2018/00678; A61B 2018/00702; A61B 2018/00708; A61B 2018/00714; A61B 2018/00755; A61B 2018/00761; A61B 2018/00779; A61B 2018/00791; A61B 2018/00845; A61B 2018/00875; A61B 2018/0088; A61B 2018/00916; A61B 2018/00928; A61B 2018/00994; A61B 2018/126; A61B 2018/1452; A61B 2018/1457; A61B 2018/1467
See application file for complete search history.

(56) References Cited

U.S. PATENT DOCUMENTS

| | | | |
|---|---|---|---|
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,231,565 B1 | 5/2001 | Tovey et al. |
| 6,283,981 B1 | 9/2001 | Beaupre et al. |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,057,498 B2 | 11/2011 | Robertson |
| 8,058,771 B2 | 11/2011 | Giordano et al. |
| 8,366,727 B2 | 2/2013 | Witt et al. |
| 8,460,326 B2 | 6/2013 | Houser et al. |
| 8,461,744 B2 | 6/2013 | Wiener et al. |
| 8,479,969 B2 | 7/2013 | Shelton, IV |
| 8,512,365 B2 | 8/2013 | Wiener et al. |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV et al. |
| 8,844,789 B2 | 9/2014 | Shelton, IV et al. |
| 8,939,974 B2 | 1/2015 | Boudreaux et al. |
| 9,017,326 B2 | 4/2015 | DiNardo et al. |
| 9,089,327 B2 | 7/2015 | Worrell et al. |
| 9,161,803 B2 | 10/2015 | Yates et al. |
| 9,192,431 B2 | 11/2015 | Woodruff et al. |
| 9,237,921 B2 | 1/2016 | Messerly et al. |
| 9,301,759 B2 | 4/2016 | Spivey et al. |
| 9,402,682 B2 | 8/2016 | Worrell et al. |
| 9,439,668 B2 | 9/2016 | Timm et al. |
| 9,545,253 B2 | 1/2017 | Worrell et al. |
| 9,572,622 B2 | 2/2017 | Shelton, IV et al. |
| 9,681,884 B2 | 6/2017 | Clem et al. |
| 9,724,118 B2 | 8/2017 | Schulte et al. |
| 10,194,972 B2 | 2/2019 | Yates et al. |
| 10,617,463 B2 | 4/2020 | McHenry et al. |
| 10,729,458 B2 | 8/2020 | Stoddard et al. |
| 10,813,684 B2 | 10/2020 | Worrell et al. |
| 10,945,778 B2 | 3/2021 | Weisenburgh et al. |
| 10,945,779 B2 | 3/2021 | Weisenburgh et al. |
| 11,033,316 B2 | 6/2021 | Estera |
| 11,051,866 B2 | 7/2021 | Estera et al. |
| 11,058,472 B2 | 7/2021 | Lesko et al. |
| 11,129,661 B2 | 9/2021 | Leuck et al. |
| 11,229,473 B2 | 1/2022 | Clauda |
| 11,229,474 B2 | 1/2022 | Nott et al. |
| 11,229,475 B2 | 1/2022 | Asher et al. |
| 11,234,750 B2 | 2/2022 | Leuck et al. |
| 11,259,856 B2 | 3/2022 | Krumm et al. |
| 11,266,455 B2 | 3/2022 | Sawhney |
| 11,278,340 B2 | 3/2022 | Asher et al. |
| 11,304,741 B2 | 4/2022 | Leuck et al. |
| 2007/0282332 A1 | 12/2007 | Witt et al. |
| 2009/0036914 A1 | 2/2009 | Houser |
| 2010/0036405 A1 | 2/2010 | Giordano et al. |
| 2011/0087212 A1 | 4/2011 | Aldridge et al. |
| 2012/0078243 A1 | 3/2012 | Worrell et al. |
| 2012/0116379 A1 | 5/2012 | Yates et al. |
| 2012/0116391 A1 | 5/2012 | Houser et al. |
| 2012/0199633 A1 | 8/2012 | Shelton, IV et al. |
| 2013/0267975 A1 | 10/2013 | Timm et al. |
| 2013/0282003 A1 | 10/2013 | Messerly et al. |
| 2013/0296908 A1 | 11/2013 | Schulte et al. |
| 2013/0324991 A1 | 12/2013 | Clem et al. |
| 2015/0141981 A1 | 5/2015 | Price et al. |

(56)　　　　　References Cited

U.S. PATENT DOCUMENTS

| | | | |
|---|---|---|---|
| 2015/0257780 | A1 | 9/2015 | Houser et al. |
| 2016/0022305 | A1 | 1/2016 | Lamping et al. |
| 2016/0058492 | A1 | 3/2016 | Yates et al. |
| 2016/0270840 | A1 | 9/2016 | Yates et al. |
| 2016/0287316 | A1 | 10/2016 | Worrell et al. |
| 2016/0310204 | A1 | 10/2016 | McHenry et al. |
| 2017/0000516 | A1 | 1/2017 | Stulen et al. |
| 2017/0000541 | A1 | 1/2017 | Yates et al. |
| 2017/0000542 | A1 | 1/2017 | Yates et al. |
| 2017/0000554 | A1 | 1/2017 | Yates et al. |
| 2017/0056056 | A1 | 3/2017 | Wiener et al. |
| 2022/0202465 | A1 | 6/2022 | Nott et al. |
| 2022/0202466 | A1 | 6/2022 | Clauda et al. |

FOREIGN PATENT DOCUMENTS

| | | |
|---|---|---|
| CN | 104244850 A | 12/2014 |
| CN | 204542303 U | 8/2015 |
| EP | 1839599 A1 | 10/2007 |
| JP | 2001-157685 A | 6/2001 |
| JP | 2015-515331 A | 5/2015 |
| JP | 2016-510638 A | 4/2016 |

OTHER PUBLICATIONS

Chinese First Office Action and Search Report dated Aug. 24, 2022, for Application No. 201880033825.X, 7 pages.
Chinese First Office Action and Search Report dated Aug. 29, 2022, for Application No. 201880034190.5, 12 pages.
Chinese First Office Action and Search Report dated Aug. 17, 2022, for Application No. 201880034192.4, 8 pages.
Chinese First Office Action and Search Report dated Sep. 19, 2022, for Application No. 201880034247.1, 8 pages.
Chinese First Office Action and Search Report dated Sep. 2, 2022, for Application No. 201880034248.6, 10 pages.
Indian Examination Report dated Feb. 7, 2022, for Application No. 201917043416, 5 pages.
Indian Examination Report dated Feb. 8, 2022, for Application No. 201917043014, 6 pages.
Indian Examination Report dated Feb. 14, 2022, for Application No. 201917044159, 7 pages.
Indian Examination Report dated Feb. 7, 2022, for Application No. 201917044324, 6 pages.
Indian Examination Report dated Jun. 13, 2022, for Application No. 201917042775, 7 pages.
Japanese Office Action dated Nov. 15, 2022, for Application No. 2019-564405, 4 pages.
Japanese Final Office Action dated Aug. 29, 2023, for Application No. 2019-564405, 3 pages.
Japanese Final Office Action dated Nov. 8, 2022, for Application No. 2019-564410, 2 pages.

Japanese Decision of Refusal dated Sep. 13, 2022, for Application No. 2019-564428, 3 pages.
Japanese Decision of Refusal dated Sep. 6, 2022, for Application No. 2019-564437, 5 pages.
Japanese Final Office Action dated Oct. 18, 2022, for Application No. 2019-564438, 3 pages.
Japanese Office Action dated Nov. 7, 2023, for Application No. 2023-001046, 6 pages.
Japanese Office Action dated Oct. 3, 2023, for Application No. 2023-002955, 5 pages.
European Examination Report dated Jun. 28, 2021, for Application No. 18729278.4, 4 pages.
European Examination Report dated Jun. 29, 2021, for Application No. 18731583.3, 4 pages.
European Examination Report dated Jun. 29, 2021, for Application No. 18731584.1, 4 pages.
European Examination Report dated Jun. 30, 2021, for Application No. 18731585.8, 4 pages.
European Examination Report dated Jan. 11, 2022, for Application No. 18769823.8, 4 pages.
International Search Report and Written Opinion dated Jul. 30, 2018, for International Application No. PCT/US2018/033301, 13 pages.
International Search Report and Written Opinion dated Jan. 24, 2019, for International Application No. PCT/US2018/033303, 20 pages.
International Search Report and Written Opinion dated Aug. 23, 2018, for International Application No. PCT/US2018/033305, 16 pages.
International Search Report and Written Opinion dated Sep. 3, 2018, for International Application No. PCT/US2018/033306, 17 pages.
International Search Report and Written Opinion dated Aug. 17, 2018, for International Application No. PCT/US2018/033309, 16 pages.
International Search Report and Written Opinion dated Aug. 23, 2018, for International Application No. PCT/US2018/033311, 16 pages.
Japanese Notification of Reasons for Refusal dated May 10, 2022, for Application No. 2019- 564405, 5 pages.
Japanese Notification of Reasons for Refusal dated Jul. 5, 2022, for Application No. 2019- 564410, 4 pages.
Japanese Notification of Reasons for Refusal dated May 10, 2022, for Application No. 2019- 564427, 4 pages.
Japanese Notification of Reasons for Refusal dated Apr. 12, 2022, for Application No. 2019- 564428, 4 pages.
Japanese Notification of Reasons for Refusal dated Apr. 12, 2022, for Application No. 2019- 564437, 5 pages.
Japanese Notification of Reasons for Refusal dated Jun. 28, 2022, for Application No. 2019- 564438, 4 pages.
U.S. Appl. No. 62/509,336, entitled "Control Algorithm for Surgical Instrument with Ultrasonic and Electrosurgical Modalities," filed May 22, 2017.
U.S. Appl. No. 62/509,351, entitled "Ultrasonic Instrument with Electrosurgical Features," filed May 22, 2017.

1210

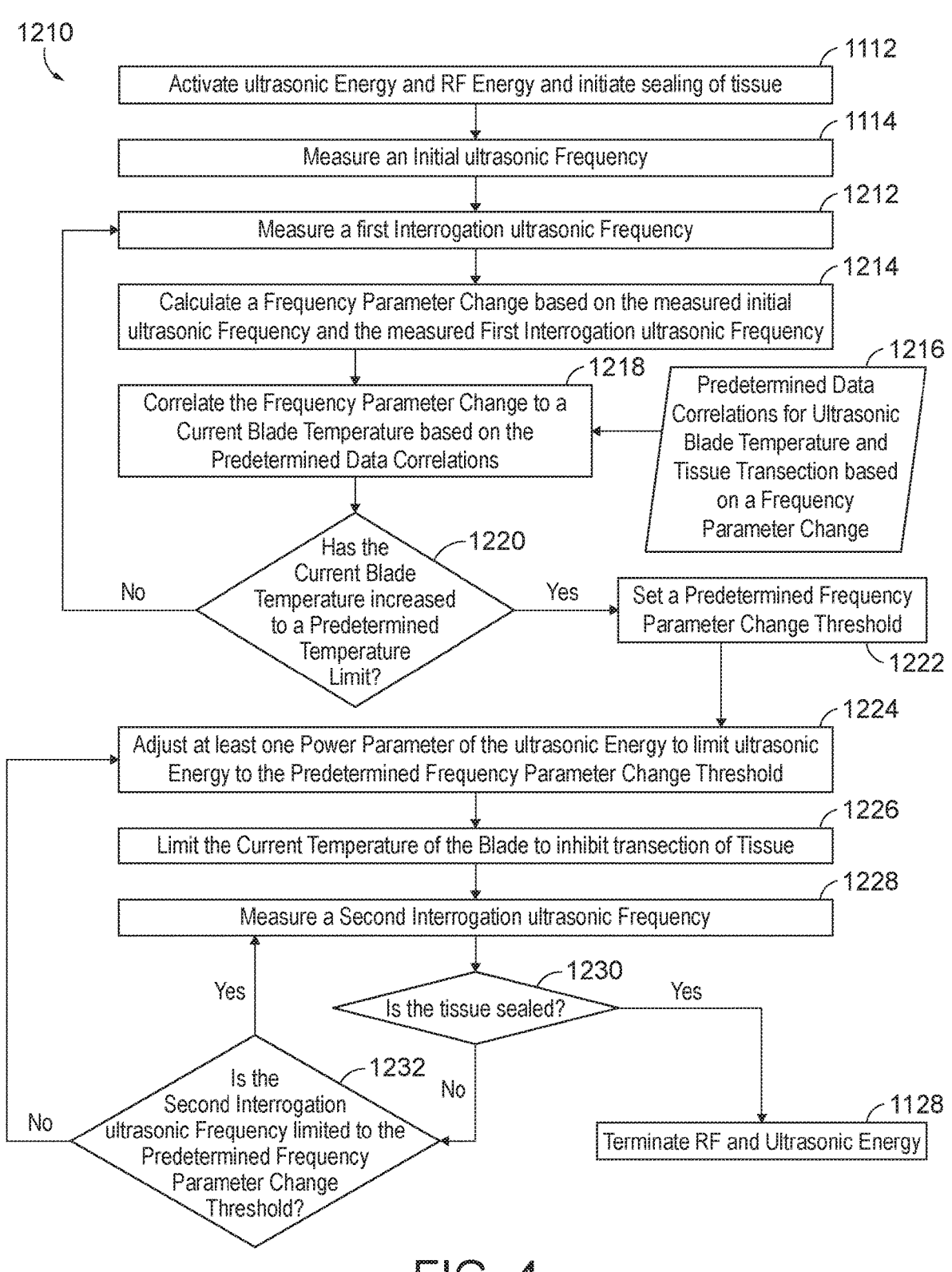

1112

Activate ultrasonic Energy and RF Energy and initiate sealing of tissue

1114

Measure an Initial ultrasonic Frequency

1212

Measure a first Interrogation ultrasonic Frequency

1214

Calculate a Frequency Parameter Change based on the measured initial ultrasonic Frequency and the measured First Interrogation ultrasonic Frequency

1218

Correlate the Frequency Parameter Change to a Current Blade Temperature based on the Predetermined Data Correlations

1216

Predetermined Data Correlations for Ultrasonic Blade Temperature and Tissue Transection based on a Frequency Parameter Change

1220

Has the Current Blade Temperature increased to a Predetermined Temperature Limit?

No

Yes

Set a Predetermined Frequency Parameter Change Threshold

1222

1224

Adjust at least one Power Parameter of the ultrasonic Energy to limit ultrasonic Energy to the Predetermined Frequency Parameter Change Threshold

1226

Limit the Current Temperature of the Blade to inhibit transection of Tissue

1228

Measure a Second Interrogation ultrasonic Frequency

1230

Is the tissue sealed?

Yes

Yes

No

1232

Is the Second Interrogation ultrasonic Frequency limited to the Predetermined Frequency Parameter Change Threshold?

No

No

1128

Terminate RF and Ultrasonic Energy

FIG. 4

COMBINATION ULTRASONIC AND ELECTROSURGICAL INSTRUMENT WITH ADJUSTABLE ENERGY MODALITIES AND METHOD FOR LIMITING BLADE TEMPERATURE

CROSS-REFERENCE TO RELATED APPLICATION

This application is a continuation of U.S. patent application Ser. No. 17/572,003, entitled "Combination Ultrasonic and Electrosurgical Instrument with Adjustable Energy Modalities and Method for Limiting Blade Temperature," filed Jan. 10, 2022, and published as U.S. Pat. Pub. No. 2022/0202465, and issued as U.S. Pat. No. 11,737,804 on Aug. 29, 2023, which is a continuation of U.S. patent application Ser. No. 15/967,775, entitled "Combination Ultrasonic and Electrosurgical Instrument with Adjustable Energy Modalities and Method for Limiting Blade Temperature," filed May 1, 2018, and issued as U.S. Pat. No. 11,229,474 on Jan. 25, 2022, which claims priority to U.S. Provisional Pat. App. No. 62/509,336, entitled "Control Algorithm for Surgical Instrument with Ultrasonic and Electrosurgical Modalities," filed May 22, 2017, the disclosure of which is incorporated by reference herein.

BACKGROUND

Ultrasonic surgical instruments utilize ultrasonic energy for both precise cutting and controlled coagulation. Ultrasonic energy cuts and coagulates by vibrating a blade in contact with tissue. Vibrating at frequencies of approximately 55.5 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit such energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No.

7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, issued as U.S. Pat. No. 11,141,213 on Oct. 12, 2021, the disclosure of which is incorporated by reference herein.

While various types of ultrasonic surgical instruments and electrosurgical instruments, including combination ultrasonic-electrosurgical devices, have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts a flowchart of a version of the method of controlling the blade temperature of FIG. 3.

Figure 1:
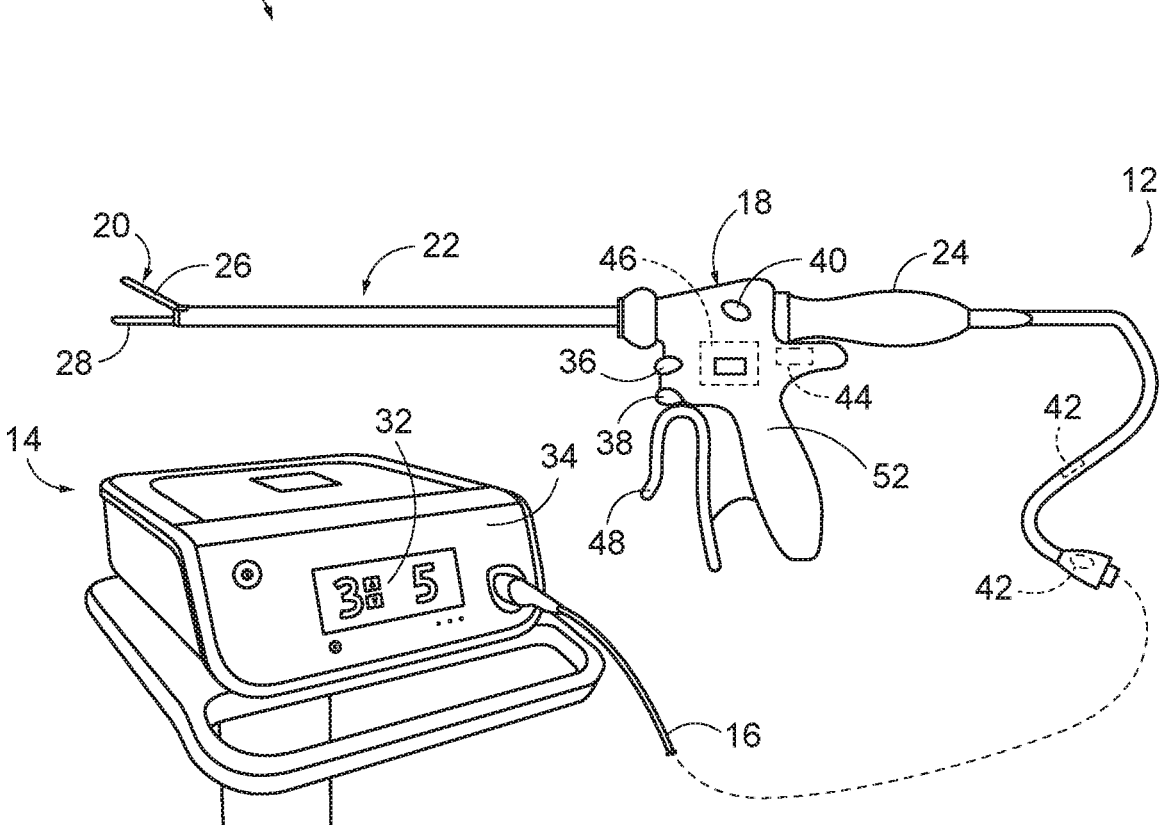
FIG. 1 depicts a schematic view of an exemplary ultrasonic surgical instrument including a shaft assembly and a handle assembly operatively connected to an ultrasonic generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical System

FIG. 1 illustrates one example of a surgical system (10) including a surgical instrument (12) and a generator (14) coupled via a cable (16). Surgical instrument (12) has a proximally positioned handle assembly (18), which may also be referred to as a handpiece, a distally positioned end effector (20), a shaft assembly (22) extending therebetween, and an ultrasonic transducer (24). End effector (20) generally includes a clamp arm (26) pivotally connected relative to an ultrasonic blade (28) and configured to pivot from an open position of an open configuration to a closed position of a closed configuration as discussed below in greater detail. Ultrasonic blade (28) is acoustically coupled with ultrasonic transducer (24) via an acoustic waveguide (not shown) for providing ultrasonic energy to ultrasonic blade (28). In addition, end effector (20) further includes a plurality of RF electrodes (30) positioned therealong for contacting the tissue in either the open or closed position as desired by a clinician. Generator (14) operatively connects to ultrasonic blade (28) and RF electrodes (30) to respectively provide ultrasonic energy and RF energy to ultrasonic blade (28) and RF electrodes (30) to thereby cut and/or seal the tissue is use.

In some versions, clamp arm (26) has two or more electrodes (30). In some such versions, electrodes (30) of clamp arm are capable of applying bipolar RF energy to tissue. In some such versions, ultrasonic blade (28) remains electrically neutral, such that ultrasonic blade (28) is not part of the RF circuit. In some other versions, ultrasonic blade (28) forms part of the RF circuit, such that ultrasonic blade (28) cooperates with one or more electrodes (30) of clamp arm (26) to apply bipolar RF energy to tissue. By way of example only, some versions of clamp arm (26) may have just one electrode (30) that serves as an active pole for RF energy; while ultrasonic blade (28) provides a return pole for RF energy. Thus, the term "electrodes (30)" should be read to include versions where clamp arm (26) has only one single electrode.

It should be understood that terms such as "proximal" and "distal" are used herein with reference to surgical instrument (12). Thus, end effector (20) is distal with respect to the more proximal handle assembly (18). It will be further appreciated that for convenience and clarity, spatial terms such as "upper" and "lower" are used herein with respect to the drawings. However, surgical instruments are used in many orientations and positions, and these terms are not intended to be limiting and absolute. Likewise, terms such as "instrument" and "device" as well as "limit" and "cap" may be used interchangeably.

A. Exemplary Generator

With reference to FIG. 1, generator (14) drives a combination surgical instrument (12) with both ultrasonic and RF energies. Generator (14) is shown separate from surgical instrument (12) in the present example, but, alternatively, generator (14) may be formed integrally with surgical instrument (12) to form a unitary surgical system. Generator (14) generally includes an input device (32) located on a front panel (34) of generator (14). Input device (32) may have any suitable device that generates signals suitable for programming the operation of generator (32). For example, in operation, the clinician may program or otherwise control operation of generator (32) using input device (32) (e.g., by one or more processors contained in the generator) to control the operation of generator (14) (e.g., operation of the ultrasonic generator drive circuit (not shown) and/or RF generator drive circuit (not shown)).

In various forms, input device (32) includes one or more buttons, switches, thumbwheels, keyboard, keypad, touch screen monitor, pointing device, remote connection to a general purpose or dedicated computer. In other forms, input device (32) may having a suitable user interface, such as one or more user interface screens displayed on a touch screen monitor. Accordingly, the clinician may selectively set or program various operating parameters of the generator, such as, current (I), voltage (V), frequency (f), and/or period (T) of a drive signal or signals generated by the ultrasonic and RF generator drive circuits (not shown). Specifically, in the present example, generator (32) is configured to deliver various power states to the surgical instrument (10) that include, but are not necessarily limited to, only ultrasonic energy, only RF energy, and a combination of ultrasonic and RF energies, which simultaneously powers ultrasonic blade (28) and RF electrodes (30). It will be appreciated that input device (32) may have any suitable device that generates signals suitable for programming the operation of generator (14) and should not be unnecessarily limited to input device (32) shown and described herein.

By way of example only, generator (14) may comprise a GEN04 or GEN11 sold by Ethicon Endo-Surgery, Inc. of Cincinnati, Ohio. In addition, or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

B. Exemplary Surgical Instrument

Surgical instrument (10) of the present example shown in FIG. 1 includes a plurality of energy inputs, which are more particularly referred to herein as an upper button (36), lower button (38), and side button (40). By way of example, upper button (36) is configured to direct generator (14) to power ultrasonic transducer (24) with a maximum ultrasonic energy output, whereas lower button (38) is configured to direct generator (14) to power ultrasonic transducer (24) with a lower ultrasonic energy output. By way of further example, side button (40) is configured to direct generator (14) to power ultrasonic transducer (24) with a pulsed energy output, such as 5 continuous signals and 5 or 4 or 3 or 2 or 1 pulsed signals. In one or more examples, the specific drive signal configuration directed by energy inputs may be controlled and/or based upon EEPROM settings in generator (14) and/or user power level selection(s). By way of further example, surgical instrument (10) may include a two-button configuration for selectively directing ultrasonic and RF energies as described herein. Various examples of instruments having two-button input configurations are described in various patent references cited herein. In any case, it will be appreciated that the invention described herein is not intended to be unnecessarily limited to a particular input button, switch, etc. to the extent that any form of input may be so used.

Surgical instrument (12) further includes a first data circuit (42) and a second data circuit (44) in communication with generator (14). For example, first data circuit (42) indicates a burn-in frequency slope. Additionally or alternatively, any type of information may be communicated to second data circuit (42) for storage therein via a data circuit interface (e.g., using a logic device). Such information may comprise, for example, an updated number of operations in which surgical instrument (12) has been used and/or dates and/or times of its usage. In other examples, second data circuit (44) may transmit data acquired by one or more sensors (e.g., an instrument-based temperature sensor). In still other examples, second data circuit (44) may receive data from generator (14) and provide an indication to a clinician (e.g., an LED indication or other visible indication) based on the received data to and/or from surgical instrument (12). In the present example, second data circuit (44) stores information about the electrical and/or ultrasonic properties of an associated transducer (24) and/or end effector (20), which includes data measured and collected from ultrasonic blade (28) and/or RF electrodes (30).

To this end, various processes and techniques described herein are performed by a controller (46), which includes internal logic. In one example, controller (46) has at least one processor and/or other controller device in communication with generator (14), ultrasonic blade (28), RF electrodes (30), and other inputs and outputs described herein for monitoring and performing such processes and techniques. In one example, controller (46) has a processor configured to monitor user input provided via one or more inputs and capacitive touch sensors. Controller (46) may also include a touch screen controller to control and manage the acquisition of touch data from a capacitive touch screen.

Figure 2A:
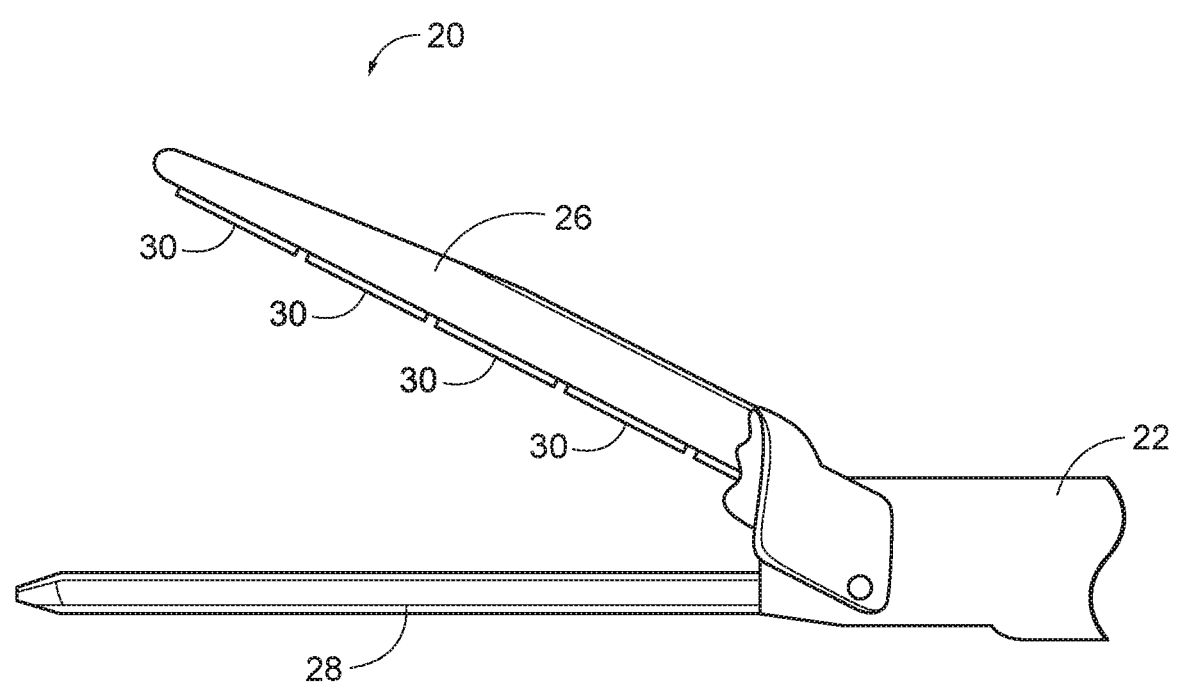
FIG. 2A depicts a side view of an end effector of the ultrasonic surgical instrument of FIG. 1 showing the end effector in an open configuration for receiving tissue of a patient.
Figure 2B:
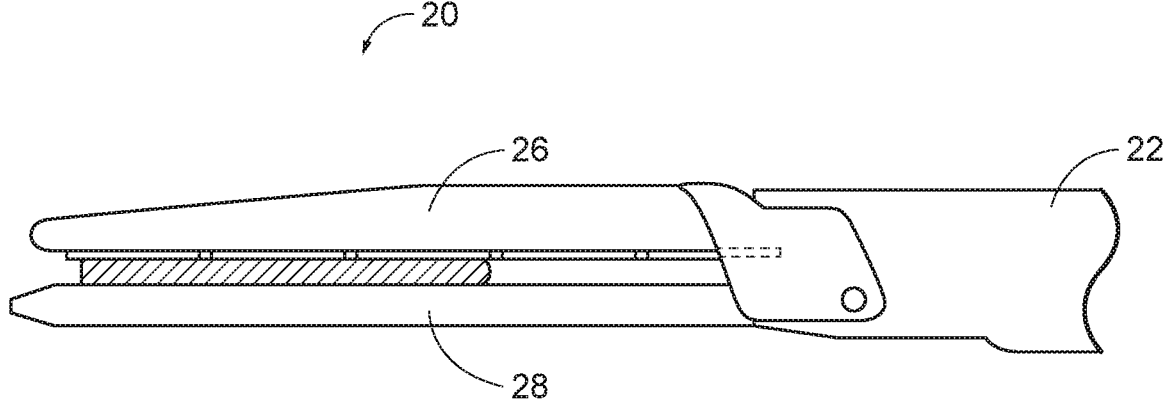
FIG. 2B depicts the side view of the end effector of FIG. 2A, but with the end effector in a closed configuration for clamping the tissue of the patient.

With reference to FIGS. 1-2B, handle assembly (18) further includes a trigger (48) operatively connected to clamp arm (26). Trigger (48) and clamp arm (26) are generally biased toward the unactuated, open configuration. However, selectively manipulating trigger (48) proximally pivots clamp arm (26) toward ultrasonic blade (28) from the open position to the closed position. As used in the present example, clamp arm (26) and ultrasonic blade (28) may also be generally referred to respectively as upper and lower jaws of surgical instrument (12). In the open position, clamp arm (26) and ultrasonic blade (28) are configured to receive the tissue, whereas clamp arm (26) is configured to clamp tissue against ultrasonic blade (28) for grasping, sealing, and/or cutting the tissue.

Ultrasonic blade (28) ultrasonically vibrates to seal and/or cut the tissue, whereas RF electrodes (30) provide electrical power to the tissue. RF electrodes (30) of the present example are all electrically similar electrodes with ultrasonic blade (28) also electrically connected as a return electrode. As used therein, the term "electrode" may thus apply to both RF electrodes (30) and ultrasonic blade (28) with respect to the RF electrical circuit. Without tissue, the electrical circuit from RF electrodes (30) to ultrasonic blade (28) is open, whereas the electrical circuit is closed by the tissue between RF electrode (30) and ultrasonic blade (28) in use. RF electrodes (30) may be activated to apply RF energy alone or in combination with ultrasonic activation of ultrasonic blade (28). For example, activating only RF electrodes (30) to apply RF energy alone may be used for spot coagulating without concern for inadvertently cutting tissue with ultrasonically activated ultrasonic blade (28). However, the combination of ultrasonic energy and RF energy may be used for sealing and/or cutting tissue to achieve any combination of diagnostic or therapeutic effects, various examples of which will be described below in greater detail.

As noted above, generator (14) is a single output generator that can deliver power through a single port to provide both RF and ultrasonic energy such that these signals can be delivered separately or simultaneously to end effector (20) for cutting and/or sealing tissue. Such a single output port generator (14) has a single output transformer with multiple taps to provide power, either for RF or for ultrasonic energy, to end effector (20) depending on the particular treatment being performed on the tissue. For example, generator (14) may deliver energy with higher voltage and lower current to drive ultrasonic transducer (24), with lower voltage and higher current as required to drive RF electrodes (30) for sealing tissue, or with a coagulation waveform for spot coagulation using either monopolar or bipolar electrosurgical electrodes. The output waveform from generator (14) can be steered, switched, or filtered to provide the desired frequency to end effector (20) of surgical instrument (12).

II. Blade Temperature Control

While ultrasonic blade (28) of FIG. 1 generally begins at an initial, room temperature upon an initial application of ultrasonic energy to tissue, the temperature tends to increase with each successive use, particularly when successive uses are over a relatively short time. Increasing temperatures of ultrasonic blade (28) tend to affect sealing and transection of the tissue in generally any method of operating surgical system (10), such as those described herein, particularly with respect to ultrasonic energy. More particularly, relatively higher temperatures tend to increase the likelihood of inadvertently transecting the tissue while sealing or even transecting the tissue too quickly prior to sealing and may not be accounted for in operation. While such effects may be trivial in some tissue treatments, adjustments to one or more electrical parameters of ultrasonic energy as described below are configured to limit the temperature of ultrasonic blade (28) for providing greater consistency in successive applications of ultrasonic energy to tissue. Such temperature limits to ultrasonic blade (28) are also configured to preserve the useful life of the clamp pad of clamp arm (26), which may be damaged by relatively high temperatures.

Figure 3:
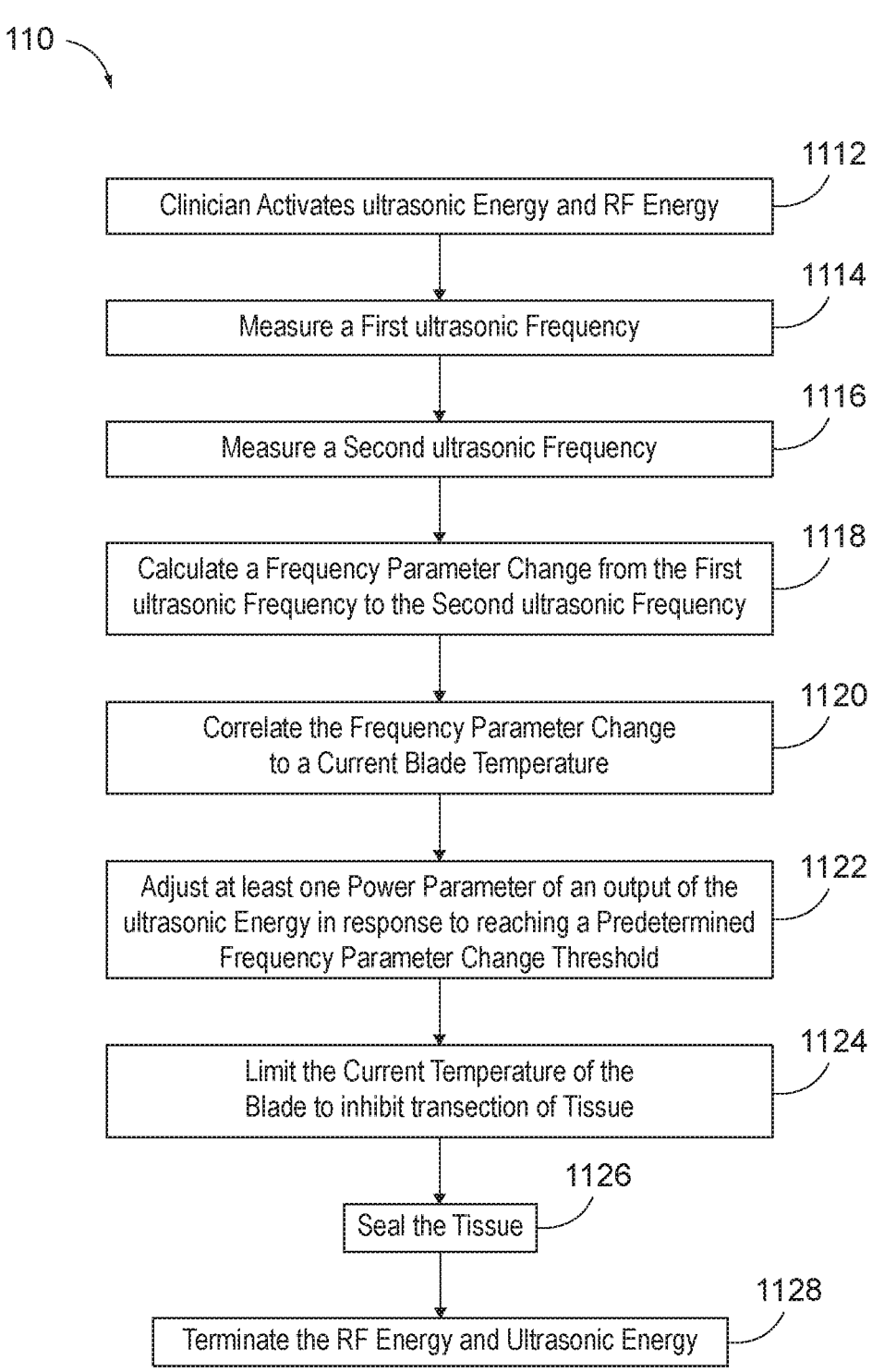
FIG. 3 depicts a flowchart of a high-level method of controlling a blade temperature of the ultrasonic surgical system of FIG. 1.

In the present example, FIG. 3 illustrates a method (1110) of, to at least some extent, controlling a temperature of ultrasonic blade (28) of surgical system (10) of FIG. 1 in use by monitoring changing ultrasonic frequencies due to temperature fluctuations to limit the temperature to an upper temperature limit. The clinician initially activates ultrasonic energy and RF energy in a step (1112) at an initial time, $T_o$, and applies the energy to tissue as described herein. Simultaneously, controller (46) interrogates ultrasonic blade (28) with a measurement of a first ultrasonic frequency at the initial time, $T_o$, and stores the first ultrasonic frequency measurement in a step (1114). After the first ultrasonic frequency measurement in step (1114), controller (46) again interrogates ultrasonic blade (28) with another measurement of a second ultrasonic frequency at a following time, $T_1$, and stores the second ultrasonic frequency measurement in a step (1116). Each of the first and second ultrasonic frequencies is accessed and applied to a calculation of a frequency parameter change from the first ultrasonic frequency to the second ultrasonic frequency in a step (1118). In one example, the frequency parameter change may be calculated based on a baseline frequency measured and stored in the EEPROM during production.

Controller (46) compares the calculated frequency parameter change to prior data of ultrasonic frequencies and correlates the calculated frequency parameter change from step (1118) to a current blade temperature in a step (1120). Based on the current blade temperature, controller (46) adjusts at least one electrical power parameter of an output of the ultrasonic energy in response to reaching a predetermined frequency parameter change threshold in a step (1122) and thereby limit current temperature of ultrasonic blade (28) in a step (1124). In one example, RF and ultrasonic energies continued to be applied in view of the adjusted electrical parameters until the tissue is sealed in a step (1126), while inhibiting transection of the tissue and/or reducing damage to clamp arm (26). In another example, the output of ultrasonic energy is terminated while RF energy continues to be applied in view of the adjusted electrical parameters until the tissue is sealed. Once the tissue is sealed, RF and ultrasonic energies are terminated. While the above description of method (1110) includes measurement and adjustments related to ultrasonic energy, it will be appreciated that such measurements and adjustments are not intended to be unnecessarily limited to only ultrasonic energy.

Figure 5:
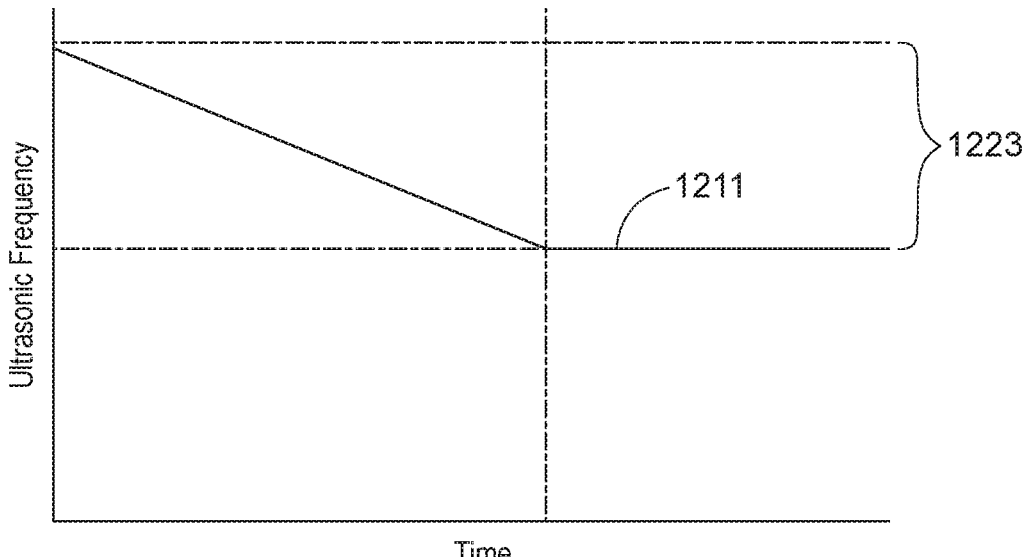
FIG. 5 depicts a graph of ultrasonic frequency of the ultrasonic energy for the version in FIG. 4 with an ultrasonic frequency cap.

FIG. 4 illustrates a more particular version (1210) of the method (1110) (see FIG. 3) discussed above with one example of ultrasonic frequency measurements represented by reference numeral (1211) in FIG. 5. Version (1210) of the present example begins with activation of ultrasonic and RF energies to initiate sealing in step (1112) while simultaneously measuring initial ultrasonic frequency in step (1114). Controller (46) then measures a first interrogation ultrasonic frequency of ultrasonic blade (28) in a step (1212) followed by a calculation of a frequency parameter change based on the initial ultrasonic frequency of step (1114) and the first interrogation ultrasonic frequency of step (1212) in a step (1214). Stored predetermined data correlations (1216) of blade temperature to frequency parameter change that are configured to inhibit tissue transection are accessed by controller (46) in a step (1218). Step (1218) thereby correlates the frequency parameter change of step (1214) based on the predetermined data correlations (1216) to a current blade temperature in real-time.

A step (1220) compares the current blade temperature from step (1218) to a predetermined temperature limit for ultrasonic blade (28) to determine whether the current blade temperature has increased to at least the predetermined temperature. In the event that the current blade temperature has not increased to the predetermined blade temperature limit, step (1212) through step (1220) repeatedly loop until the current blade temperature is at least the predetermined temperature. Once the current blade temperature is at least the predetermined blade temperature in step (1220), controller (46) sets a predetermined frequency parameter change threshold on the ultrasonic energy in a step (1222). In the present example, ultrasonic frequencies (1211) tend to decrease with increasing temperature as illustrated in FIG. 5, which identifies an exemplary predetermined frequency parameter change threshold (1223), and may be monitored by a difference between at least two ultrasonic frequency measurements (1211) over time or a slope of ultrasonic frequency. In response to this setting, a step (1224) adjusts at least one power parameter of the ultrasonic energy to limit ultrasonic energy to the predetermined frequency parameter change threshold (1223) and, in turn, limits the current blade temperature to inhibit transection of the tissue in a step (1226).

Controller (46) then measures a second interrogation ultrasonic frequency in a step (1228) followed by a determination of whether the tissue is sealed in a step (1230). In the event that the tissue is sealed, controller (46) terminates ultrasonic and RF energies in step (1128) as discussed above. However, in the event that the tissue is not yet sealed, controller (46) determines if the second interrogation ultrasonic frequency is limited to the predetermined frequency parameter change threshold (1223) in a step (1232). If the second interrogation ultrasonic frequency is limited to the predetermined frequency parameter change threshold (1223), then step (1228) and step (1230) repeat. If the second interrogation ultrasonic frequency exceeds the predetermined frequency parameter change threshold (1223), then further adjustment and limiting per step (1224) and step (1226) followed by step (1228) and step (1230) repeat. These repetition loops based on step (1232) continue until the tissue is sealed in step (1230) followed by RF and ultrasonic energy termination in step (1128).

Furthermore, in one or more examples, transfer functions based on frequency measurements (1211) and/or frequency slope may also be configured to control the output of the ultrasonic energy in order to control blade temperature. In any case, blade temperature control may also be configured to reduce and/or minimize temperature differential between ultrasonic blade (28) and clamp arm (26) by further controlling RF energy applied to the tissue via RF electrodes (30) for relatively even temperature changes across tissue from ultrasonic blade (28) to clamp arm (26).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of limiting an ultrasonic blade temperature of a surgical instrument with an ultrasonic blade configured to apply ultrasonic energy to tissue, the method comprising: (a) increasing the temperature of the ultrasonic blade toward an upper temperature limit; (b) adjusting at least one power parameter of the ultrasonic energy in response to reaching a predetermined frequency parameter change threshold in the ultrasonic blade; and (c) limiting the temperature of the ultrasonic blade to the upper temperature limit.

Example 2

The method of Example 1, further comprising: (a) measuring a first ultrasonic frequency of the ultrasonic blade; (b) measuring a second ultrasonic frequency of the ultrasonic blade after measuring the first ultrasonic frequency; and (c) calculating a frequency parameter change between the measured first and second ultrasonic frequencies of the ultrasonic blade.

Example 3

The method of Example 2, wherein the first ultrasonic frequency of the ultrasonic blade is an initial ultrasonic frequency of the ultrasonic blade.

Example 4

The method of any one or more of Examples 1 through 3, further comprising correlating the frequency parameter change of the ultrasonic blade to the temperature of the ultrasonic blade.

Example 5

The method of Example 4, wherein correlating the frequency parameter change further includes correlating the frequency parameter change of the ultrasonic blade to the temperature of the ultrasonic blade based on a plurality of predetermined data correlations of blade temperature to frequency parameter stored on a controller of the surgical instrument.

Example 6

The method of any one or more of Examples 1 through 5, further comprising determining that the temperature of the ultrasonic blade has increased to the upper temperature limit.

Example 7

The method of any one or more of Examples 1 through 6, wherein limiting the temperature of the ultrasonic blade further includes limiting the temperature of the ultrasonic blade to thereby inhibit transection of a tissue.

Example 8

The method of any one or more of Examples 1 through 7, further comprising measuring a third ultrasonic frequency of the ultrasonic blade.

Example 9

The method of Example 8, further comprising determining that a tissue engaged with the ultrasonic blade is not sealed.

Example 10

The method of Example 9, further comprising: (a) determining that the third ultrasonic frequency of the ultrasonic blade reached the predetermined frequency parameter change threshold; and (b) further adjusting the at least one power parameter of the ultrasonic energy in response to reaching the predetermined frequency parameter change threshold in the ultrasonic blade.

Example 11

The method of Example 9, further comprising: (a) determining that the third ultrasonic frequency of the ultrasonic blade is less than the predetermined frequency parameter change threshold; and (b) remeasuring the third ultrasonic frequency of the ultrasonic blade.

Example 12

The method of any of Example 8, further comprising determining that a tissue engaged with the ultrasonic blade is sealed.

Example 13

The method of Example 12, further comprising terminating the ultrasonic energy based on the determination that the tissue engaged with the ultrasonic blade is sealed.

Example 14

The method of any one or more of Examples 1 through 13, wherein limiting the temperature of the ultrasonic blade further includes inhibiting damage to a clamp arm configured to compress a tissue against the ultrasonic blade.

Example 15

The method of any one or more of Examples 1 through 14, further comprising setting the predetermined frequency parameter change threshold.

Example 16

A method of determining an ultrasonic blade temperature of a surgical instrument having an ultrasonic blade configured to be driven by an ultrasonic energy, the method comprising: (a) measuring a first ultrasonic frequency of the ultrasonic blade; (b) measuring a second ultrasonic frequency of the ultrasonic blade after measuring the first ultrasonic frequency; (c) calculating a frequency parameter change between the measured first and second ultrasonic frequencies of the ultrasonic blade; and (d) correlating the frequency parameter change of the ultrasonic blade to the temperature of the ultrasonic blade to thereby determine the temperature of the ultrasonic blade.

Example 17

The method of Example 16, wherein correlating the frequency parameter change further includes correlating the frequency parameter change of the ultrasonic blade to the temperature of the ultrasonic blade based on a plurality of predetermined data correlations of blade temperature to frequency parameter stored on a controller of the surgical instrument.

Example 18

An ultrasonic surgical instrument, comprising: (a) an end effector configured to actuate from a first configuration to a second configuration, including: (i) an ultrasonic blade configured to selectively apply ultrasonic energy to tissue, and (ii) a jaw movably positioned relative to the ultrasonic blade and configured to move between an open position and a closed position, wherein the jaw and ultrasonic blade in the open position are configured to receive tissue, and wherein the jaw and ultrasonic blade in the closed position are configured to clamp the tissue; (b) a shaft assembly projecting proximally from the end effector; (c) a body projecting proximally from the shaft assembly, wherein the body includes an energy input operatively connected to the ultrasonic blade; and (d) a controller operatively connected to the ultrasonic blade and configured to measure an ultrasonic frequency of the ultrasonic blade, wherein the controller has a memory including a plurality of predetermined data correlations that correlate changes in measured ultrasonic frequency of the ultrasonic blade to a blade temperature of the ultrasonic blade, wherein the controller is configured to correlate the predetermined data correlations to the blade temperature of the ultrasonic blade.

Example 19

The ultrasonic surgical instrument of Example 18, wherein the controller is further configured to limit the blade temperature to an upper temperature limit.

Example 20

The ultrasonic surgical instrument of Example 18, wherein the memory further includes a predetermined frequency parameter threshold, and wherein the controller is configured to adjust at least one power parameter of the ultrasonic energy and limit the measured ultrasonic frequency of the ultrasonic blade to the predetermined frequency parameter threshold for limiting the temperature of the blade to an upper temperature limit.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

Any one or more of the teaching, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on May 1, 2018, published as U.S. Pub. No. 2018/0333182 on Nov. 22, 2018; U.S. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018; U.S. patent application Ser. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 2018; U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018; and/or U.S. patent application Ser. No. 15/967,784, entitled "Combination Ultrasonic and Electrosurgical Instrument and Method for Sealing Tissue in Successive Phases," filed on May 1, 2018, published as U.S. Pub. No. 2018/0333190 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed on May 1, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on May 1, 2018, issued as U.S. Pat. No. 11,058,472 on Jul. 13, 2021; U.S. patent application Ser. No. 15/967,759, entitled "Combination Ultrasonic and Electrosurgical Instrument Having Ultrasonic Waveguide With Distal Overmold Member," filed on May 1, 2018, issued as U.S. Pat. No. 11,051,866 on Jul. 6, 2021; U.S. patent application Ser. No. 15/967,761, entitled "Combination Ultrasonic and Electrosurgical System Having Generator Filter Circuitry," filed on May 1, 2018, published as U.S. Pub. No. 2018/0333184 on Nov. 22, 2018; and/or U.S. patent application Ser. No. 15/967,764, entitled "Combination Ultrasonic and Electrosurgical System Having EEPROM and ASIC Components," filed on May 1, 2018, published as U.S. Pat. No. 11,129,661 on Sep. 28, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism,"

issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

We claim:

1. An ultrasonic surgical instrument, comprising:
   (a) an end effector including:
      (i) an ultrasonic blade configured to selectively apply ultrasonic energy to tissue, and
      (ii) a jaw movably positioned relative to the ultrasonic blade and configured to move between an open position and a closed position, wherein the jaw and ultrasonic blade in the open position are configured to receive tissue, and wherein the jaw and ultrasonic blade in the closed position are configured to clamp the tissue;
   (b) a controller operatively connected to the ultrasonic blade and configured to:
      (i) set a predetermined frequency parameter change threshold based at least on a plurality of predetermined data correlations of blade temperature to frequency parameter; and
      (ii) adjust at least one power parameter of the ultrasonic energy in response to reaching the predetermined frequency parameter change threshold in the ultrasonic blade to limit the ultrasonic energy to the predetermined frequency parameter change threshold for limiting blade temperature during use.

2. The ultrasonic surgical instrument of claim 1, further comprising a shaft assembly projecting proximally from the end effector.

3. The ultrasonic surgical instrument of claim 2, further comprising a body projecting proximally from the shaft assembly.

4. The ultrasonic surgical instrument of claim 3, wherein the body includes an energy input operatively connected to the ultrasonic blade.

5. The ultrasonic surgical instrument of claim 1, wherein plurality of predetermined data correlations of blade temperature to frequency parameter are stored on the controller.

6. The ultrasonic surgical instrument of claim 1, wherein the controller is further configured to measure an interrogation ultrasonic frequency and further adjust the at least one power parameter of the ultrasonic energy based on the measured interrogation ultrasonic frequency for further limiting blade temperature during use.

7. The ultrasonic surgical instrument of claim 1, wherein the controller is configured to limit blade temperature of the ultrasonic blade to thereby inhibit transection of the tissue while sealing the tissue.

8. The ultrasonic surgical instrument of claim 1, wherein the controller is configured to calculate a frequency parameter change while applying ultrasonic energy to the tissue.

9. The ultrasonic surgical instrument of claim 8, wherein the controller is configured to correlate the frequency parameter change to a current blade temperature.

10. An ultrasonic surgical instrument, comprising:

(a) an end effector including:

(i) an ultrasonic blade configured to selectively apply ultrasonic energy to tissue, and (ii) a jaw movably positioned relative to the ultrasonic blade and configured to move between an open position and a closed position, wherein the jaw and ultrasonic blade in the open position are configured to receive tissue, and wherein the jaw and ultrasonic blade in the closed position are configured to clamp the tissue; and (b) a controller operatively connected to the ultrasonic blade and having a plurality of predetermined data correlations of blade temperature to frequency parameter stored thereon, wherein the controller is configured to:

(i) calculate a frequency parameter change while applying ultrasonic energy to the tissue, and (ii) correlate the frequency parameter change to a current blade temperature based at least on the plurality of predetermined data correlations of blade temperature to frequency parameter.

11. The ultrasonic surgical instrument of claim 10, further comprising a shaft assembly projecting proximally from the end effector.

12. The ultrasonic surgical instrument of claim 11, further comprising a body projecting proximally from the shaft assembly.

13. The ultrasonic surgical instrument of claim 12, wherein the body includes an energy input operatively connected to the ultrasonic blade.

14. The ultrasonic surgical instrument of claim 10, wherein the controller is configured to limit blade temperature to inhibit transection of the tissue during use.

15. The ultrasonic surgical instrument of claim 14, wherein the controller is configured to adjust at least one power parameter of the ultrasonic energy to limit the ultrasonic energy and thereby limit blade temperature to inhibit transection of the tissue during use.

16. The ultrasonic surgical instrument of claim 10, wherein the controller is configured to determine that the tissue engaged with the ultrasonic blade is not sealed.

17. The ultrasonic surgical instrument of claim 16, wherein the controller is configured to determine that the tissue engaged with the ultrasonic blade is sealed.

18. An ultrasonic surgical instrument, comprising:

(a) an end effector including:

(i) an ultrasonic blade configured to selectively apply ultrasonic energy to tissue, and (ii) a jaw movably positioned relative to the ultrasonic blade and configured to move between an open position and a closed position, wherein the jaw and ultrasonic blade in the open position are configured to receive tissue, and wherein the jaw and ultrasonic blade in the closed position are configured to clamp the tissue; and (b) a controller operatively connected to the ultrasonic blade, wherein the controller is configured to:

(i) determine that a current blade temperature has increased to a predetermined temperature limit based at least on a plurality of predetermined data correlations of blade temperature to frequency parameter, and (ii) limit the current blade temperature to the predetermined temperature limit while sealing the tissue.

19. The ultrasonic surgical instrument of claim 18, wherein the plurality of predetermined data correlations of blade temperature to frequency parameter are stored on the controller.

20. The ultrasonic surgical instrument of claim 18, wherein the controller is configured to adjust at least one power parameter of the ultrasonic energy to limit the ultrasonic energy and thereby limit the current blade temperature to inhibit transection of the tissue during use.

\* \* \* \* \*